United States Patent [19]

Friese et al.

[11] Patent Number: 5,630,920
[45] Date of Patent: May 20, 1997

[54] ELECTROCHEMICAL SENSOR FOR DETERMINING THE OXYGEN CONCENTRATION IN GAS MIXTURES

[75] Inventors: Karl-Hermann Friese, Leonberg; Hans-Martin Wiedenmann, Stuttgart; Frank Stanglmeier, Moeglingen, all of Germany

[73] Assignee: Robert Bosch GmbH, Stuttgart, Germany

[21] Appl. No.: 545,865

[22] PCT Filed: Feb. 28, 1995

[86] PCT No.: PCT/DE95/00253

§ 371 Date: Jan. 19, 1996

§ 102(e) Date: Jan. 19, 1996

[87] PCT Pub. No.: WO95/25276

PCT Pub. Date: Sep. 21, 1995

[30] Foreign Application Priority Data

Mar. 14, 1994 [DE] Germany ............. 44 08 361.0

[51] Int. Cl.[6] .................................................. G01N 27/26
[52] U.S. Cl. ............. 204/424; 204/425; 204/426; 204/427; 204/428; 204/429; 204/421
[58] Field of Search ................................. 204/424, 425, 204/426, 427, 428, 429, 421

[56] References Cited

U.S. PATENT DOCUMENTS

| | | |
|---|---|---|
| 3,941,673 | 3/1976 | Takao et al. ............. 204/424 |
| 4,547,281 | 10/1985 | Wang et al. ............. 204/424 |
| 4,863,583 | 9/1989 | Kurachi et al. ............. 204/429 |
| 5,314,604 | 5/1994 | Friese et al. ............. 204/429 |
| 5,411,644 | 5/1995 | Neukermans ............. 204/427 |
| 5,427,672 | 6/1995 | Böcker et al. ............. 204/429 |
| 5,486,279 | 1/1996 | Friese et al. ............. 204/429 |

FOREIGN PATENT DOCUMENTS

| | | |
|---|---|---|
| 2291357 | 6/1976 | France . |
| 2451031 | 10/1980 | France . |
| 2304464 | 8/1974 | Germany . |
| 0466020 | 1/1992 | Germany . |
| 525317 | 10/1982 | Japan . |
| 331050 | 9/1989 | Japan . |

*Primary Examiner*—Bruce F. Bell
*Attorney, Agent, or Firm*—Spencer & Frank

[57] ABSTRACT

An electrochemical sensor for determining the oxygen concentration in gas mixtures is proposed. The sensor has a solid electrolyte (10) with oxygen ionic conductivity, which has a measuring electrode (11) that does not catalyze establishment of equilibrium of the gas mixture and is exposed to the gas mixture. The measuring electrode (11) contains platinum and bismuth. The effect of these materials is that the free oxygen contained in the gas mixture is preferentially adsorbed, without reacting with the other gas components such as CO and HC.

14 Claims, 1 Drawing Sheet

ELECTROCHEMICAL SENSOR FOR DETERMINING THE OXYGEN CONCENTRATION IN GAS MIXTURES

PRIOR ART

The invention is based on an electrochemical sensor for determining the oxygen concentration in gas mixtures.

In the case of known electrochemical sensors for determining oxygen concentration, the emf at the electrodes is measured, a large voltage being produced if the lambda value of the gas mixture is smaller than the stoichiometric ratio. In this case, a material, for example platinum, that catalyzes establishment of equilibrium of the gas mixture is used for the electrode exposed to the gas to be measured. The effect of the catalyzing property of platinum is that the free oxygen occurring in the gas mixture binds to the oxidizable components in the gas mixture, as a result of which the sensor is also sensitive to oxidizable gas components. However, the cross-sensitivity of electrochemical sensors has a disruptive effect in particular application cases.

It is, for example, possible to monitor the operational integrity of catalytic convertors in exhaust emission control systems of internal-combustion engines by measuring the oxygen contained in the exhaust gas downstream of the catalyst in the exhaust gas flow direction. If the catalytic convertor is not operational, then the oxygen in the exhaust gas downstream of the catalyst remains incompletely converted, and oxidizable and reducible fuel components which are still unconverted are found in the exhaust gas. Incomplete conversion means that the residual oxygen content in the exhaust gas is substantially higher than that which corresponds to thermodynamic equilibrium. The sensor according to the invention is, for example, intended to respond to such an increased residual oxygen content. Care must therefore be taken for it to be possible to measure the changes in the oxygen partial pressure at the three-phase boundary of the measuring electrode. To this end, it is known from DE-A 23 04 464 to produce an electrode that does not catalyze establishment of equilibrium of the gas mixture from gold or silver. The effect of these electrode materials is that a competitive reaction between the oxygen and the oxidizable or reducible gas components takes place at the electrode. As a result, even when high lambda values have been tuned, the free oxygen entrained in the exhaust gas is extensively converted by the competitive reaction with, for example, CO, so that only little oxygen reaches the three-phase boundary of the measuring electrode, the result of which is that an approximately equally high positive potential remains obtained from low to high lambda values. In the case of a correctly operating catalytic convertor, the oxygen is converted by the catalyst, so that at least approximately the thermodynamic equilibrium pressure exists downstream of the catalytic converter, the result of which is that the potential difference at the measuring electrode is reduced and a lambda jump occurs like in the case of a conventional lambda probe. With decreasing degree of conversion by the catalytic converter, the lambda jump is shifted to higher lambda values. A disadvantage with this sensor is that no potential difference occurs with lambda values tuned to <1 (rich exhaust gas). The sensor is therefore unsuitable for monitoring a catalytic convertor in this lambda range.

ADVANTAGES OF THE INVENTION

The sensor according to the invention has the advantage that the oxygen in non-equilibrium gas mixtures can be measured, with the greatest possible exclusion of cross-sensitivity to oxidizable gas components. The sensor is particularly suitable for monitoring the degree of conversion by catalytic convertors in exhaust emission control systems of internal-combustion engines with exhaust gases tuned to lambda values of <1. Conclusions regarding the ageing of the catalyst can be drawn from the degree of convergence by the catalytic convertor.

According to other features of the present invention, advantageous further developments and improvements of the sensor according to the invention are possible. The platinum-bismuth measuring electrode uses the properties of bismuth, which has a strong inclination to oxygen adsorption, it even being possible for oxygen to be adsorbed dissociatively. In combination with platinum, bismuth prevents adsorption of other gas components such as, for example, CO in favor of good oxygen adsorption. As a result, the catalysis of oxidation of CO and HC, which occur in exhaust gases of internal-combustion engines, is impeded or fully suppressed, so that a mixed potential is set up at the measuring electrode. The measuring electrode designed in this way essentially reacts with oxygen and, in this respect, constitutes a non-equilibrium electrode or mixed-potential electrode. It was possible to establish the action of bismuth to inhibit the catalysis of platinum within a range having a bismuth content of 1 to 50 mol % relative to the total amount of platinum and bismuth. It was possible to ascertain particularly favorable properties with regard to mixed-potential formation and reaction times with a bismuth proportion of 5 to 20 mol % relative to the total amount of bismuth and platinum.

BRIEF DESCRIPTION OF THE DRAWINGS

Two exemplary embodiments of the invention are represented in the drawing and explained in more detail in the description below.

EXEMPLARY EMBODIMENTS

Figure 1:
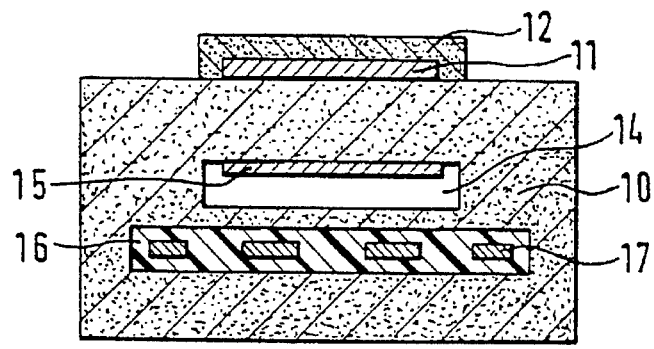
FIG. 1 shows a cross section through a sensor according to a first exemplary embodiment.

The sensor according to FIG. 1 consists of a solid electrolyte 10 with oxygen ionic conductivity, for example $Y_2O_3$-stabilized $ZrO_2$, on which a first measuring electrode 11, exposed to the gas mixture, having an overlying porous protective layer 12 is applied. The protective layer 12 consists, for example, of $Al_2O_3$. A reference channel 14, in which a reference electrode 15 is positioned adjacent to the measuring electrode 11, is provided in the solid electrolyte 10. A heater 17 embedded in electrical insulation 16 is furthermore integrated in the solid electrolyte 10. The heater 17 is produced in the form of a resistive heating element.

The measuring electrode 11 is a porous platinum Cermet electrode which is printed onto the solid electrolyte 10, for example by means of screen printing. The reference electrode 15 is likewise platinum Cermet electrode which has been applied, for example likewise using the screen-printing process, onto a corresponding solid electrolyte film before laminating the solid electrolyte 10. The sensor present according to FIG. 1, having the platinum Cermet electrodes 11, 15 and the heater 17 is sintered at approximately 1400° C. after printing of the corresponding solid electrolyte film and lamination.

After sintering, a bismuth-containing paste is applied to the measuring electrode 11, for example using a brush. The sensor with the bismuth layer applied to the measuring electrode 11 is then heated to a temperature of approximately 800° to 900° C. in an oxygen atmosphere. When selecting the heating temperature of the bismuth layer, care should be taken that the bismuth does not evaporate before it binds to the platinum or forms a stable oxide on the surface. After application of the bismuth layer or after production of a bismuth-platinum compound in the measuring electrode 11, the protective layer 12 is applied, for example by means of plasma spraying.

Figure 2:
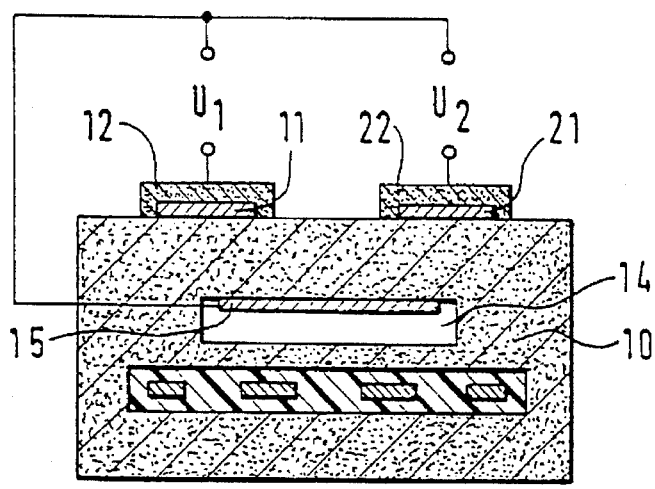
FIG. 2 shows a cross section through a sensor according to a second exemplary embodiment, the sensor being provided with two electrodes exposed to the gas mixture.

In the case of the sensor represented in FIG. 2, the sensor described in FIG. 1 is supplemented with a second measuring electrode 21 exposed to the gas mixture, the second measuring electrode 21 being likewise covered with a porous protective layer 22. In contrast to the first measuring electrode 11, the second measuring electrode 21 is an electrode that catalyzes establishment of equilibrium of the gas mixture. An electrode material that achieves such an action is, for example, platinum or a platinum alloy with rhodium or palladium. At the second measuring electrode 21, the oxygen content partial pressure is set to the thermodynamic equilibrium pressure by oxidation.

Figure 3:
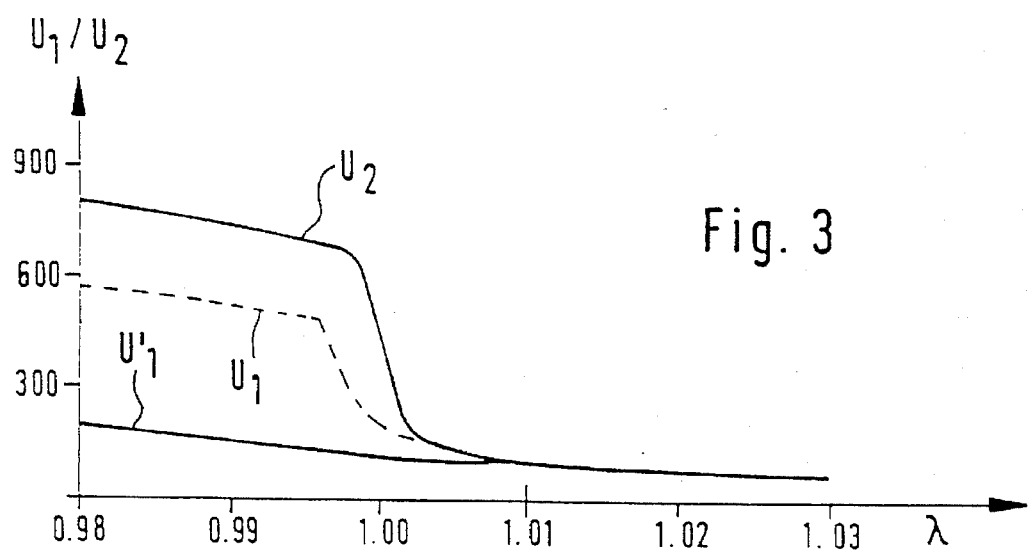
FIG. 3 shows a characteristic curve of the sensor according to FIG. 2.

The characteristic lines, represented in FIG. 3, of the sensor according to FIG. 2 show a measurement signal U1 from the catalytically inactive measuring electrode 11 and a measurement signal U2 from the catalytically active measuring electrode 21, measured downstream in the exhaust gas flow direction from a catalytic convertor (not shown). The emf of the catalytically inactive measuring electrode 11 was also recorded using a sensor arranged upstream in the exhaust gas flow direction from the catalyst, and is represented as the measurement signal U1'. The measurement signal U1' recorded upstream from the catalyst characterizes the characteristic line of a catalyst having an efficiency of 0%, i.e. it indicates total catalytic convertor failure. Because of the oxygen dissociating at the catalytically inactive measuring electrode 11, there is a small potential difference between the reference electrode 15 and the measuring electrode 11.

The measurement signal U2 recorded at the catalytically active measuring electrode 21 has a lambda jump in the equilibrium state at lambda=1. At the catalytically active measuring electrode 21, the oxygen partial pressure is always vanishingly small, independently of the state of the catalytic convertor used for afterburning. In this case the oxygen partial pressure corresponds to the thermodynamic equilibrium pressure because the electrode material of the measuring electrode 21 guarantees at least approximately complete conversion with oxygen of the oxidizable components.

If the catalytic convertor is no longer effective, then the oxygen partial pressure in the exhaust gas increases. In this case nothing changes at the three-phase boundary of the catalytically active measuring electrode 21, because the electrode material furthermore causes at least approximately complete conversion of the oxidizable components, before the gas reaches the three-phase boundary. At the catalytically inactive measuring electrode 11, in contrast, the oxygen partial pressure depends on the catalytic activity of the catalytic convertor. If the catalytic convertor is fully effective, then the exhaust gas is at least approximately in the equilibrium state downstream of the catalytic convertor. No oxygen at all, or only very little, can consequently be dissociated by the material of the measuring electrode 11, as a result of which a large potential difference is set up at the measuring electrode 11. In this case the measurement signal U1 from the catalytically inactive measuring electrode 11 approximately follows the profile of the measurement signal U2 from the catalytically active measuring electrode 21. When the degree of conversion by the catalytic convertor drops, the oxygen partial pressure in the exhaust gas increases, so that the potential difference at the three-phase boundary of the catalytically inactive electrode 11 decreases. The curve represented as a broken line shows the profile of the measurement signal U1 when the efficiency of the catalytic converter is approximately 90%.

The sensor according to the invention is therefore suitable for monitoring the operational integrity of catalytic convertors which are fitted in exhaust systems of internal-combustion engines that are tuned to a rich exhaust gas (lamda<1).

According to the invention, the bismuth may be fully or partially replaced by antimony or lead.

We claim:

1. A sensor for determining the oxygen concentration in gas mixtures, having a solid electrolyte, with oxygen ionic conductivity, which has a measuring electrode that does not catalyze establishment of equilibrium of the gas mixture and is exposed to the gas mixture, wherein there is added to a platinum-containing measuring electrode (11) a material which is capable of inhibiting the catalytic action of the measuring electrode (11), in such a way that it is possible to set up at the measuring electrode (11) a potential which at least approximately corresponds to the free oxygen content.

2. The sensor as claimed in claim 1, wherein the material added to the platinum-containing measuring electrode (11) is bismuth.

3. The sensor as claimed in claim 2, wherein the bismuth content is from 1 to 50 mol % relative to the total amount of platinum and bismuth.

4. The sensor as claimed in claim 3, wherein the bismuth content is from 5 to 20 mol % relative to the total amount of platinum and bismuth.

5. The sensor claimed in claim 4, wherein the bismuth is fully or partially replaced by antimony.

6. The sensor as claimed in claim 4, wherein the bismuth is fully or partially replaced by lead.

7. The sensor as claimed in claim 3, wherein the bismuth is fully or partially replaced by antimony.

8. The sensor as claimed in claim 3, wherein the bismuth is fully or partially replaced by lead.

9. The sensor as claimed in claim 1, wherein another measuring electrode (21), exposed to the gas mixture, is provided which has an action catalyzing establishment of equilibrium of the gas mixture.

10. The sensor as claimed in claim 1, wherein a reference electrode (15), exposed to a reference gas, is provided.

11. The sensor as claimed in claim 1, wherein the material added to the platinum-containing measuring electrode (11) is antimony.

12. The sensor as claimed in claim 1, wherein the material added to the platinum-containing measuring electrode (11) is bismuth and antimony.

13. The sensor as claimed in claim 1, wherein the material added to the platinum-containing measuring electrode (11) is lead.

14. The sensor as claimed in claim 1, wherein the material added to the platinum-containing measuring electrode (11) is bismuth and lead.

* * * * *